United States Patent [19]

Finlayson

[11] Patent Number: 5,551,444
[45] Date of Patent: Sep. 3, 1996

[54] FLEXIBLE GUIDEWIRE WITH RADIOPAQUE OUTER COIL AND NON-RADIOPAQUE INNER COIL

[75] Inventor: Maureen Finlayson, Acton, Mass.

[73] Assignee: Radius Medical Technologies, Inc., Maynard, Mass.

[21] Appl. No.: 456,037

[22] Filed: May 31, 1995

[51] Int. Cl.⁶ .................................................. A61B 5/00
[52] U.S. Cl. ............................................ 128/772; 128/657
[58] Field of Search ................................ 128/657, 772; 604/95, 164, 170, 280, 282

[56] References Cited

U.S. PATENT DOCUMENTS

| | | |
|---|---|---|
| 3,789,841 | 2/1974 | Antoshkiw . |
| 4,538,622 | 9/1985 | Samson et al. . |
| 4,719,924 | 1/1988 | Crittenden et al. ............... 128/657 X |
| 4,884,579 | 12/1989 | Engelson . |
| 4,917,104 | 4/1990 | Rebell ................................ 128/772 |
| 4,934,380 | 6/1990 | de Toledo .......................... 128/772 |
| 5,065,769 | 11/1991 | de Toledo .......................... 128/657 X |
| 5,069,217 | 12/1991 | Fleischhacker, Jr. . |
| 5,111,829 | 5/1992 | de Toledo . |
| 5,129,890 | 7/1992 | Bates et al. . |
| 5,165,421 | 11/1992 | Fleischhacker et al. . |
| 5,345,945 | 9/1994 | Hodgson et al. . |
| 5,346,508 | 9/1994 | Hastings . |
| 5,353,808 | 10/1994 | Viera ................................. 128/657 X |
| 5,376,083 | 12/1994 | Mische .............................. 128/772 X |
| 5,377,690 | 1/1995 | Berthiaume . |

FOREIGN PATENT DOCUMENTS

| | | | |
|---|---|---|---|
| 92/19151 | 11/1992 | WIPO ................................. 128/772 |
| 94/06347 | 3/1994 | WIPO ................................. 128/772 |

Primary Examiner—Sam Rimell
Attorney, Agent, or Firm—Cesari and McKenna

[57] ABSTRACT

A guidewire includes a tapered core, an elongated non-radiopaque inner coil that is coincident with the core and extends over a distal portion of the core, and a radiopaque outer coil that fits over a distal end of the inner coil. The inner coil tapers between its proximal end and distal end, to form a tapered distal end section. The outer diameter of the proximal end of the inner coil is the same as the outer diameter of the proximal end of the core, before its first taper, and similarly, the outer diameter of the outer coil is the same as the outer diameter of the inner coil before its taper. Accordingly, the guidewire has an essentially uniform outer diameter over its entire length. A rounded tip that acts as a deformable buffer is formed where the distal ends of the two coils and the core join. The distal end of the core is preferably flattened to provide a formable end to the guidewire. A low friction coating may be added to the wire, to facilitate movement of the wire through the arteries.

15 Claims, 2 Drawing Sheets

FLEXIBLE GUIDEWIRE WITH RADIOPAQUE OUTER COIL AND NON-RADIOPAQUE INNER COIL

FIELD OF THE INVENTION

This invention relates generally to guidewires for directing a catheter or other medical instrument through the cardiovascular system and, more particularly, to guide wires that have radiopaque distal ends.

BACKGROUND OF THE INVENTION

Guidewires for use in, for example, percutaneous transluminal coronary artery angioplasty (PTCA), must be thin and flexible enough to advance through small arteries toward the coronary artery. These wires must also be sturdy enough to be manipulated from the outside of the body, such that a distal end of the wire can be brought into contact with a selected region of the coronary artery. Further, they must be strong enough to survive a "pull test" without breaking, to ensure that they do not come apart in the body.

Prior known guidewires each essentially include a solid tapered core and an elongated non-radiopaque coil or sleeve that is coincident with and extends over a distal portion of the core. The coil or sleeve adds strength to the tapered distal end of the core, essentially without limiting its flexibility. Each of the guidewires also has a radiopaque distal end that is 1 to 3 centimeters in length. This allows the cardiologist to observe, using x-ray or fluoroscopy, the progress of the wire through the arteries. The remainder of the wire is non-radiopaque, to avoid obscuring the arteries from view.

These guidewires differ in how the radiopaque distal ends are formed, and there are essentially two types of guidewires.

One type of prior known guidewire includes a shorter radiopaque end coil that is attached to the distal end of an elongated non-radiopaque coil. The two coils have the same outer diameter and are typically made from coil wires that have the same thickness. The elongated coil is made from a material, such as stainless steel, which is relatively inexpensive. The shorter radiopaque coil is made from a precious metal, such as platinum, and is thus relatively expensive, even though it is fairly short.

A problem with this guidewire, beyond the expense of the radiopaque coil, is that it is difficult to assemble. The distal end of the elongated coil and the proximal end of the shorter coil must be held completely flush while they are welded or soldered together, to ensure a strong joint. Since these coils are each approximately 0.014 inch in diameter, it is difficult to hold them in proper alignment during the welding or soldering operation. There is also a danger that the two coils may become unattached during use. If this happens, the radiopaque coil may slide off the end of the essentially smooth core and become free in a patient's body.

Another type of prior known guidewire has at its distal end a radiopaque coil that is positioned inside the distal end of the elongated coil. This arrangement essentially prevents the radiopaque coil from sliding off the core, since the elongated coil provides a rough surface that frictionally holds the shorter coil in place. Further, this guidewire is relatively easy to assemble, since the elongated coil holds the shorter coil in place for soldering or welding once the coil is positioned within the distal end of the elongated coil.

The radiopaque coil used in the latter guidewire must be made quite small, to fit within the distal end of the elongated coil. The elongated outer coil typically has an outer diameter of approximately 0.014 inch and an inner diameter of 0.011 inch or less. Accordingly, the outer diameter of the inner radiopaque coil must be 0.010 inch or less to fit within the elongated coil. A problem with a radiopaque coil that has such a small outer diameter is that the coil is difficult to discern under x-ray or fluoroscopy. This guidewire may thus be difficult to use.

SUMMARY OF THE INVENTION

The invention is a guidewire that includes (i) a tapered center core with a proximal end and a flattened distal end, (ii) a coincident elongated non-radiopaque inner coil with a tapered distal end that extends over a distal portion of the core, and (iii) a short radiopaque outer coil that fits over the tapered distal end of the inner coil. The radiopaque outer coil has an outer diameter that is the same as the non-tapered end of the elongated coil, which is typically 0.014 inch. The outer coil can thus be readily seen under x-ray or fluoroscopy.

The distal end of the guidewire includes three layers, namely, the flattened end of the core, the tapered end of the inner coil and the outer coil. The outer coil can thus be made from a relatively thin coil wire without adversely affecting the strength of the distal end of the guidewire. Accordingly, this coil is not as expensive to manufacture as the radiopaque coil that attaches to the distal end of the non-radiopaque coil and thus must alone provide sufficient strength to the distal end of the guidewire.

More specifically, the current guidewire includes a solid wire core that tapers at several points along its length to its flattened distal end. The elongated tapered inner coil attaches at its proximal end to the core, preferably at the core's first taper, and at its distal end to the distal end of the core. Before it tapers, the inner coil has an outer diameter that is the same as the outer diameter of the proximal end of the core.

The radiopaque outer coil extends from the taper of the inner coil to the distal end of that coil. The outer coil at each of its ends is joined to both the core and the inner coil through soldering, welding or brazing. The joined distal ends of the core and coils form a deformable tip that acts essentially as a buffer.

The outer coil has the same outer diameter as the inner coil has before its taper, and thus, the same outer diameter as the proximal end of the core. Accordingly, the assembled guidewire has a substantially uniform outer diameter along its entire length.

The guidewire may be coated with a teflon, silicon, hydrophylic or other low friction coating, to allow the wire to slide more easily through the arteries.

BRIEF DESCRIPTION OF THE DRAWINGS

The above and further advantages of the invention may be better understood by referring to the following description in conjunction with the accompanying drawings, in which.

DETAILED DESCRIPTION OF AN ILLUSTRATIVE EMBODIMENT

Figure 1:
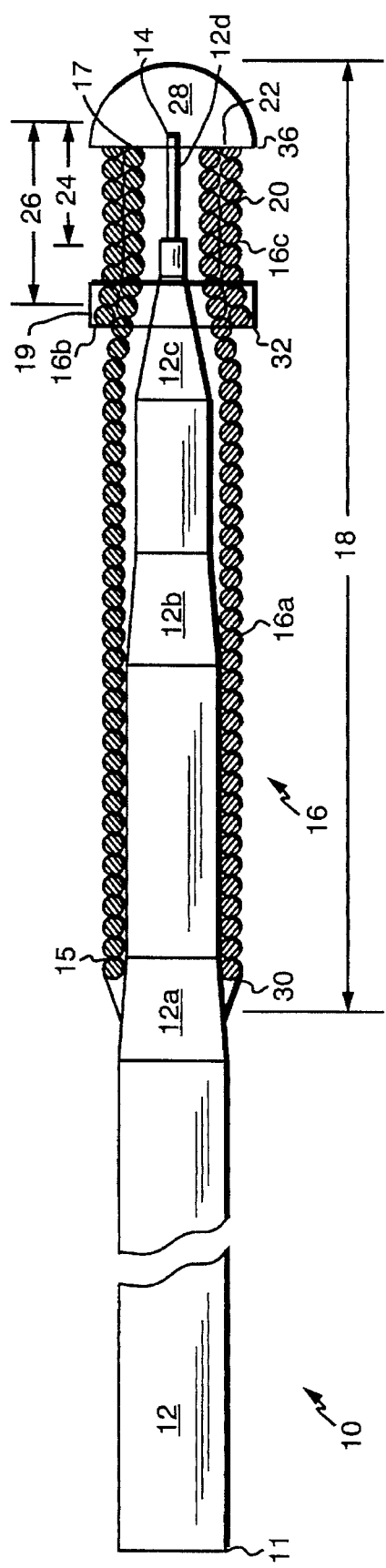
FIG. 1 is a cross-sectional view of a guidewire constructed in accordance with the invention.

Fig. 1 depicts in cross section a flexible guidewire 10 that includes a core 12, which is tapered to an essentially flattened section 12d at its distal end 14. An elongated non-radiopaque inner coil 16 is coincident with and extends over a distal portion 18 of the core 12. The non-radiopaque inner coil 16 tapers at section 16b between its proximal end 15 and its distal end 17, to form a tapered end section 16c. A radiopaque outer coil 20 fits over the tapered end section 16c of the non-radiopaque inner coil, to form a distal end 26 of the guidewire 10.

The outer diameter of the radiopaque outer coil 20 is the same as the outer diameter of the non-tapered section 16a of the inner coil, which, in turn, is the same as the outer diameter of the core 12 before its first taper 12a. The guidewire 10 thus has an essentially uniform outer diameter from its proximal end 11 to its distal end 26.

The non-radiopaque inner coil 16 attaches at its proximal end 15 to the first tapered section 12a of the core 12. The inner coil 16 may be attached to this section by, for example, welding, brazing, or soldering, as depicted in the drawing by joint 30. This coil also attaches at its tapered section 16b to both a proximal end 19 of the radiopaque outer coil 20 and a tapered section 12c of the core 12, as depicted by joint 32. The two coils 16 and 20 and the core 12 are joined at their distal ends 17, 22 and 14, by, for example, welding, brazing or soldering. This forms a rounded tip 28 that acts as a deformable buffer.

As discussed above, the end section 12d of the core is flattened. This makes a corresponding end portion 24 of the guidewire readily bendable, such that a cardiologist may shape the end 24, as necessary, to facilitate the movement of the wire along a selected artery. As necessary to achieve the desired flexibility, the spacing between the windings of the coils can be adjusted by, for example, stretching the coils.

The guidewire 10 may be coated with a silicon, teflon, hydrophilic or other low friction coating. This allows the wire to slide more easily through the artery. If the coating is teflon, it does not adhere to precious metals, and thus, the mating stops at the proximal 19 end of the outer coil 20. Accordingly, a coating other than teflon is preferably used.

Figure 2:
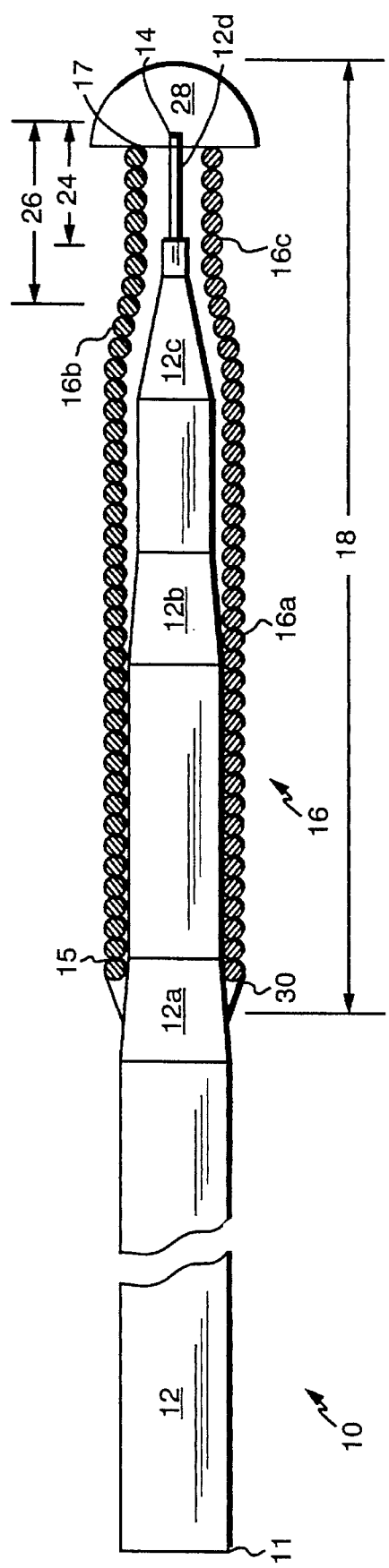
FIG. 2 is a cross-sectional view of a partially disassembled guidewire of FIG. 1.

FIG. 2 depicts in cross-section a partially disassembled wire 10. The radiopaque outer coil 20 (FIG. 1) has been removed to reveal the non-radiopaque inner coil 16 in its entirety. Accordingly, the tapered section 16b and tapered end section 16c are shown without obstruction.

Table 1 sets forth the dimensions of an exemplary embodiment of the guidewire 10. In this exemplary embodiment the guidewire 10 has an overall outer diameter of 0.014inch. The radiopaque outer coil, which has the same outer diameter, can be easily seen under x-ray and fluoroscopy.

In the exemplary embodiment, the coil wire used to make the non-radiopaque outer coil is 0.003inch in diameter and the radiopaque coil wire used to make the outer coil is 0.0015inch in diameter. Since the outer coil is layered over the inner coil, the outer coil can be made from this thinner coil wire without adversely affecting the strength of the distal end of the guidewire. This coil is thus less expensive to manufacture than the radiopaque end coil that, in prior known guidewires, attaches to the distal end of the non-radiopaque coil. The prior known end coil cannot be made of the thin coil wire since it alone must provide sufficient strength to the distal end of the guidewire.

The current guidewire is easy to assemble. An assembler slides the inner coil over the distal portion of the tapered core until the proximal end of the coil is stopped by the first taper of the core. The assembler next slides the outer coil over the tapered distal end of the inner coil, until the proximal end of the outer coil is stopped by the tapered section of the inner coil. The outer coil is then held in place on the inner coil by friction. The assembler next joins the appropriate ends of the coils to the core by soldering, brazing or welding, and forms the rounded tip. This method of assembly is easier than that used to assemble the type of guidewires in which the non-radiopaque elongated coil and the radiopaque end coil must be held with their adjacent ends flush while they are soldered or welded together. Further, the current wire is safer to use than these prior guidewires, since the outer coil is held in place by friction as well as by the weld or solder joint.

The foregoing description has been limited to a specific embodiment of this invention. It will be apparent, however, that variations and modifications may be made to the invention, with the attainment of some or all of its advantages. Therefore, it is the object of the appended claims to cover all such variations and modifications as come within the true spirit and scope of the invention.

TABLE 1

Dimensions of Exemplary Embodiment

| | |
|---|---|
| Core Outer Diameter | .014 inch |
| Overall Guidewire Length | 180 cm |
| Overall Core Taper Length | 30 cm |
| Core Taper Length (Flattened End) | 1.5 cm |
| Core Taper Outer Diameter (Flattened End) | .002 inch |
| Non-Radiopaque Coil Length | 30 cm |
| Non-Radiopaque Coil Taper Length | 3 cm |
| Non-Radiopaque Coil Taper Outer Diameter | .011 inch |
| Radiopaque Coil Length | 3 cm |
| Radiopaque Coil Outer Diameter | .014 inch |
| Coil Wire Diameter Of The Non-Radiopaque Coil | .0030 inch |
| Coil Wire Diameter Of The Radiopaque Coil | .0015 inch |

What is claimed is:

1. A guidewire for use in gaining access to an artery, the guidewire including:

A. a tapered core wire with a proximal end and a distal end and at least one tapered section between the proximal and distal ends;

B. an elongated non-radiopaque inner coil that is concentric with the core and extends over a distal portion of the core to the distal end of the core, the inner coil having a proximal end, a tapered distal end section and a distal end;

C. a radiopaque outer coil that is concentric with and fits over the tapered distal end section of the inner coil and extends to the distal end of the inner coil.

2. The guidewire of claim 1, wherein the inner coil extends from a tapered section of the core that is closest to the proximal end of the core.

3. The guidewire of claim 2 further including a rounded tip that is formed at the distal ends of the core, the inner coil, and the outer coil.

4. The guidewire of claim 2 wherein the proximal end of the inner coil is joined to the tapered section that is closest to the proximal end of the core, and the distal end of the inner coil is joined to the distal end of the core.

5. The guidewire of claim 4 wherein the proximal end of the outer coil is joined to the proximal end of the tapered end section of the inner coil, and the distal end of the outer coil is joined to the distal ends of the inner coil and the core.

6. The guidewire of claim 5, wherein the guidewire is coated with a low friction coating.

7. A guidewire for use in gaining access to an artery, the guidewire including a proximal end and a distal end, wherein the distal end of the guidewire is formed from:

A. a first layer that consists of a distal end of a tapered core wire;

B. a second layer that consists of a distal end of a non-radiopaque inner coil that is concentric with the core wire and covers the distal end of the core wire, the distal end of the inner coil being tapered to form a tapered distal end sections; and C. a third layer that consists of a distal end of a radiopaque outer coil that is concentric with the inner coil and covers the tapered distal end section of the inner coil.

8. The guidewire of claim 7 wherein the inner coil tapers at the distal end to form a tapered distal end section, and the outer coil fits over the tapered distal end section.

9. The guidewire of claim 8 wherein the inner coil has an outer diameter at its proximal end that is the same as the outer diameter of a proximal end of the core wire and the outer coil has an outer diameter that is the same as the outer diameter of the proximal end of the inner coil.

10. The guidewire of claim 9 wherein the guidewire is coated with a low friction coating.

11. A guidewire for use in gaining access to an artery, the guidewire including:

A. a tapered core wire with a proximal end and a distal end and at least one tapered section between the proximal and distal ends;

B. an elongated non-radiopaque inner coil that is concentric with the core and extends over a distal portion of the core to the distal end of the core, the inner coil having a proximal end, a tapered distal end section and a distal end, the proximal end of the inner coil being joined to the tapered section of the core that is closest to the proximal end of the core and the distal end of the inner coil being joined to the distal end of the core; and C. a radiopaque outer coil that is concentric with and extends over the tapered distal end section of the inner coil.

12. The guidewire of claim 11 further including a rounded tip that is formed at the distal ends of the core, the inner coil, and the outer coil.

13. The guidewire of claim 11 wherein the proximal end of the outer coil is joined to the proximal end of the tapered end section of the inner coil, and the distal end of the outer coil is joined to the distal ends of the inner coil and the core.

14. The guidewire of claim 13 further including a rounded tip that is formed at the distal ends of the core, the inner coil, and the outer coil.

15. The guidewire of claim 14, wherein the guidewire is coated with a low friction coating.

\* \* \* \* \*